United States Patent [19]

Conley et al.

[11] 4,303,795
[45] Dec. 1, 1981

[54] SUBSTITUTED β-ANILINO-γ-METHOXY-CROTONATES

[75] Inventors: Richard A. Conley, Annandale, N.J.; Margaret M. Lam, New York, N.Y.; Leroy B. High, Cranbury, N.J.

[73] Assignee: E. R. Squibb & Sons, Inc., Princeton, N.J.

[21] Appl. No.: 171,579

[22] Filed: Jul. 23, 1980

Related U.S. Application Data

[62] Division of Ser. No. 56,660, Jul. 11, 1979, Pat. No. 4,252,945.

[51] Int. Cl.³ ......................................... C07C 101/453
[52] U.S. Cl. .................................... 560/43; 560/22; 560/51; 560/53; 560/174; 560/21; 544/250
[58] Field of Search ............................. 560/22, 43, 21

[56] References Cited

U.S. PATENT DOCUMENTS 4,027,037  5/1977  Siegle ................................... 560/43

OTHER PUBLICATIONS

Sugiyana, Chem. Absts., 86, 89811(m), 1977.

Primary Examiner—G. T. Breitenstein
Attorney, Agent, or Firm—Lawrence S. Levinson; Burton Rodney

[57] ABSTRACT

A process is provided for preparing pyrazolo-[1,5-c]quinazoline derivatives of the structure

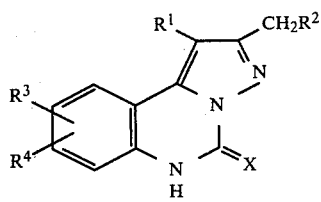

wherein X is O or S; $R^1$ is hydrogen, lower alkyl, hydroxymethyl, phenyl-lower alkyl, phenyl or phenyl substituted with halogen, lower alkyl, lower alkoxy, or trifluoromethyl; $R^2$ is lower alkoxy, phenyl-lower alkoxy, phenoxy, or phenoxy substituted with lower alkyl or lower alkoxy; and $R^3$ and $R^4$ are the same or different and are selected from the group consisting of hydrogen, alkyl of 1 to 4 carbons, alkoxy of 1 to 4 carbons, lower alkanoyloxy of 1 to 4 carbons, nitro, benzyloxy, benzyloxy having a single mono-lower alkoxy substituent, halogen, hydroxy, and trifluoromethyl, wherein quinolone compounds of the structure

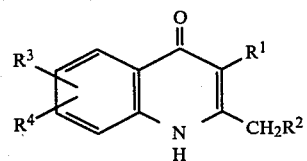

which are new intermediates, are reacted with a hydrazine compound to form a 5-(2-aminophenyl)-pyrazole which is then cyclized to the product.

In addition, the above product may be reacted with a halogen acid to form the corresponding hydroxymethyl compound.

3 Claims, No Drawings

SUBSTITUTED β-ANILINO-γ-METHOXY-CROTONATES

This is a division of application Ser. No. 56,600, filed July 11, 1979, now U.S. Pat. No. 4,252,945.

BRIEF DESCRIPTION OF THE INVENTION

The present invention relates to a process for preparing pyrazolo[1,5-c]quinazolines of the structure

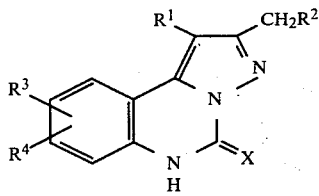

wherein

X is O or S;

$R^1$ is hydrogen, lower alkyl, hydroxymethyl, phenyl-lower alkyl, phenyl or phenyl substituted with halogen, lower alkyl, lower alkoxy, or trifluoromethyl;

$R^2$ is lower alkoxy, phenyl-lower alkoxy, phenoxy, or phenoxy substituted with lower alkyl or lower alkoxy;

$R^3$ and $R^4$ are the same or different and are selected from the group consisting of hydrogen, alkyl of 1 to 4 carbons, alkoxy of 1 to 4 carbons, lower alkanoyloxy of 1 to 4 carbons, nitro, benzyloxy, benzyloxy having a single mono-lower alkoxy substituent, halogen, hydroxy, and trifluoromethyl.

The present invention also reated to a process for preparing pyrazolo[1,5-c]quinazolines of the structure

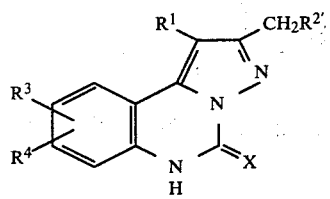

wherein $R^1$, $R^3$, $R^4$ and X are as defined above and $R^{2'}$ is CH$_2$OH or CH$_2$Hal wherein Hal is Cl, Br or F, and which process may also include the preparation of compounds of the structure

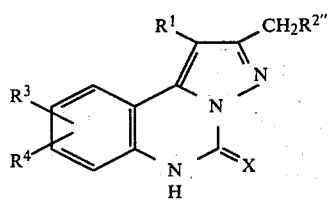

wherein $R^1$, $R^3$, $R^4$ and X are as defined above and $R^{2''}$ is lower alkanoyloxy, phenyl-lower alkanoyloxy or benzyloxy.

Essentially all of the above pyrazolo[1,5-c]-quinazolines are disclosed in U.S. Pat. Nos. 4,076,818 and 4,112,096, as well as in U.S. application Ser. No. 900,050, filed Apr. 26, 1978, now abandoned, and are useful as anti-allergy agents.

In addition, novel intermediates are also provided which are prepared in the course of carrying out the processes of the invention and have the structures

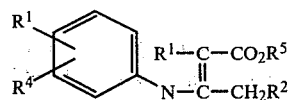

and

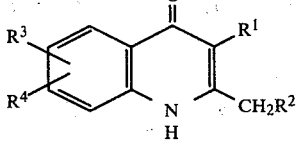

wherein $R^1$, $R^2$, $R^3$ and $R^4$ are as defined above and $R^5$ is lower alkyl.

DETAILED DESCRIPTION OF THE INVENTION

Unless otherwise indicated the term "lower alkyl" or "alkyl" as employed herein includes both straight and branched chain radicals of up to eight carbon atoms, for instance, methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, and the like.

Unless otherwise indicated, the term "lower alkoxy" or "alkoxy" includes straight and branched chain radicals which correspond to the above lower alkyl groups attached to an oxygen atom.

Unless otherwise indicated, the term "lower alkanoyl" or "alkanoyl" as employed herein includes any of the above lower alkyl groups linked to a carbonyl group.

Unless otherwise indicated, the term "substituted phenyl" includes radicals, such as lower alkyl phenyl (e.g., o-, m- or p-tolyl, ethylphenyl, butylphenyl, and the like), di(lower alkyl)phenyl (e.g., 2,4-dimethylphenyl, 3,5-diethylphenyl, and the like), halophenyl (e.g., chlorophenyl, bromophenyl, iodophenyl, fluorophenyl), lower alkoxyphenyl (e.g., methoxyphenyl or ethoxyphenyl); or trifluoromethylphenyl.

Unless otherwise indicated, the term "lower alkanoyloxy" or "alkanoyloxy" as employed herein includes any of the above defined "lower alkanoyl" or "alkanoyl" groups linked to an oxygen atom.

The process in accordance with the present invention for preparing the formula I compounds

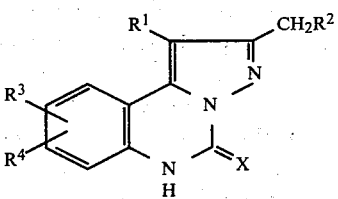

includes the steps of reacting a quinolone compound of the structure

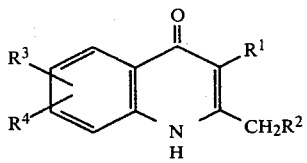

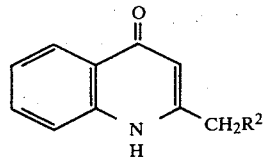

with a hydrazine compound, preferably a hydrazine dihydrohalide, such as hydrazine dihydrochloride, and hydrazine, in the presence of a high boiling solvent (for example, boiling at above about 150° C.), such as ethylene glycol or anisole, to form a 5-(2-aminophenyl)-pyrazole of the structure VI

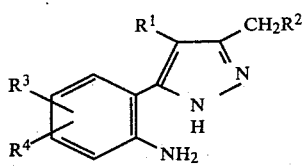

wherein $R^1$, $R^2$, $R^3$ and $R^4$ are as defined above, employing the procedures similar to those outlined in U.S. Pat. No. 3,313,815; Bowie et al, *J. Chem. Soc.* Perkin I, 1972, 1106; Field et al, *J. Org. Chem.*, 36, 2968 (1971); de Stevens et al, *Angew. Chemie*, 74, 249 (1962); and Alberti, *Gazz. Chim. Ital.*, 87, 772 (1957).

The above reaction is preferably carried out at a temperature of from about 150° to about 230° C., more preferably from about 160° to about 180° C., for a period ranging from about 3 to about 24 hours, more preferably from about 3 to about 6 hours, employing a molar ratio of V:hydrazine compound of from about 0.05:1 to about 1:1, more preferably from about 0.05:1 to about 0.2:1.

The 5-(2-aminophenyl)-pyrazole VI is then cyclized by reaction with a cyclizing agent of the structure VII CXCl₂    VII wher X is O or S (that is, phosgene or thiophosgene) or ethyl chloroformate, to form a pyrazolo[1,5-c]quinazoline of the structure I, employing procedures similar to those outlined in U.S. Pat. Nos. 3,531,482, 3,313,815 and 3,899,508, as well as in de Stevens et al, *J. Org. Chem.* 28, 1336 (1963), and the de Stevens et al, Field et al, and Bowie et al references mentioned above. The latter reaction is carried out in the presence of a basic solvent such as pyridine, triethylamine, quinoline, dimethylaniline and the like, at a temperature ranging from about 60° to about 240° C., more preferably from about 80° to about 120° C., for a period ranging from about 3 to about 24 hours and more preferably from about 12 to about 24 hours employing a molar ratio of VI to cyclizing agent of from about 0.2:1 to about 1:1, and more preferably from about 0.3:1 to about 1:1.

In preferred embodiments of the invention, the starting quinolone V will have the following structure

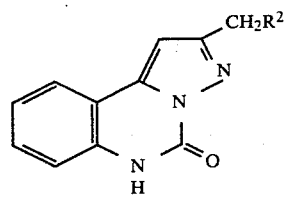

and the cyclizing agent preferably employed will be phosgene, so that the final products of structure I will have the following structure

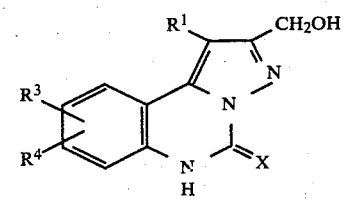

The compounds of formula II which include a $CH_2R^{2'}$ group at the 2-position, representing $CH_2OH$ or $CH_2Hal$, are prepared, in accordance with the present invention, by reacting a compound of formula I with a halogen acid such as HBr, HCl or HF, preferably in a molar ratio of I:halogen acid of within the range of from about 0.01:1 to about 1:1, and more preferably from about 0.03:1 to about 0.06:1. The above reaction may be carried out at a temperature of from about 20° to about 130° C., and more preferably from about 80° to about 120° C. and most preferably at reflux temperature for periods of about 30 minutes or less to ensure a larger proportion of hydroxymethyl compound IIa

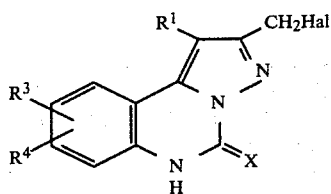

and a smaller proportion of halomethyl compound IIb

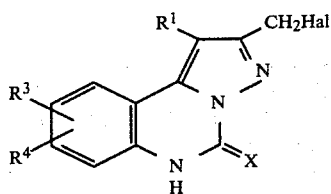

Such reaction may be carried out for a period of from about 15 minutes to about 4 hours, and preferably for about 30 minutes to about 1 hour.

In accordance with the process of the invention, a mixture of the compounds IIa and IIb may be converted to the more desirable compound IIa by simply heating the mixture at a temperature ranging from about 20° to about 100° C., and preferably from about 80° to about 100° C., in the presence of water, for periods of from about 1 hour to about 24 hours and preferably from about 4 to about 6 hours.

Alternatively, the mixture of compounds IIa and IIb may be converted to the more desirable compound IIa by reacting the mixture of compounds IIa and IIb with an alkali metal compound $$MR^{2''} \qquad \text{VIII}$$

wherein M is an alkali metal and $R^{2''}$ is lower alkanoyloxy, phenyl-lower alkanoyloxy or benzoyloxy, and the corresponding carboxylic acid $$R^{2''}H \qquad \text{IX}$$

wherein $R^{2''}$ is as above, to form the formula III compound

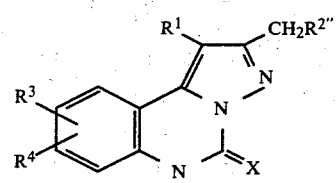

or

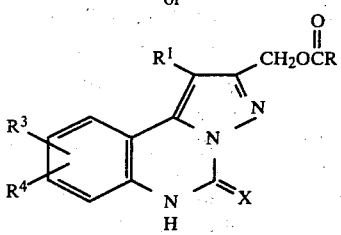

where R is lower alkyl, phenyl or phenyl-lower alkyl.

The latter reaction is preferably carried out at a temperature ranging from about 20° to about 150° C., and more preferably from about 80° to about 120° C., for a period of from about 1 to about 24 hours and preferably from about 10 to about 16 hours. The compound IIa preferably will be employed in a molar ratio to compound IX of within the range of from about 0.01:1 to about 0.1:1, and more preferably from about 0.03:1 to about 0.05:1, while the compound IIb will be employed in a molar ratio to compound VIII within the range of from about 0.2:1 to about 1:1, and more preferably from about 0.4:1 to about 0.5:1.

The formula III or IIIa compound may be converted to the hydroxymethyl compound of formula IIa by simply reacting the formula III or IIIa compound with a strong base, such as sodium hydroxide or potassium hydroxide, in the presence of a lower alkanol solvent, such as methanol or ethanol, (molar ratio of base:alkanol, preferably being from about 0.5:1 to about 0.1:1) for a period ranging from about 3 to about 24 hours and preferably from about 3 to about 6 hours and thereafter neutralizing the reaction mixture with a concentrated mineral acid, such as hydrochloric acid or sulfuric acid.

The quinolone starting material V is a new compound and may be prepared by reacting an aniline compound X

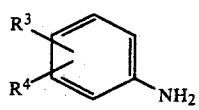

wherein $R^3$ and $R^4$ are as defined above with a carboxylic acid ester of the structure XI

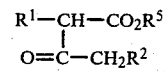

wherein $R^1$ and $R^2$ are as defined above and $R^5$ is lower alkyl, in a molar ratio of X:XI preferably of 1:1 to form an intermediate of the structure IV

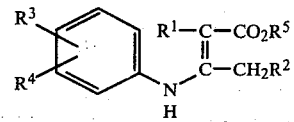

wherein $R^1$, $R^2$, $R^3$, $R^4$ and $R^5$ are as defined above. The above reaction is preferably carried out in the presence of a weak organic acid, such as acetic acid or propionic acid, and an aromatic solvent such as benzene or toluene, or hexane at a temperature ranging from about 60° to about 120° C. and preferably from about 60° to about 80° C. for a period of from about 1 hour to about 12 hours and preferably from about 2 to about 3 hours.

As indicated, the intermediate IV represents a new compound and as such forms a part of the present invention.

The quinolone compound V (also a new intermediate) is then prepared by simply reacting the intermediate IV with diphenyl ether in a molar ratio of IV:ether of from about 0.1:1 to about 0.5:1, and preferably from about 0.1:1 to about 0.2:1, at a temperature ranging from about 180° to about 270° C., and preferably from about 240° to about 260° C. for a period of from about 30 minutes to about 2 hours, and preferably from about 30 minutes to about 1 hour.

In a preferred embodiment, aniline itself (the formula X compound) is reacted with the carboxylic acid ester

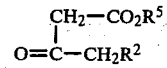

so that the intermediate IV will have the structure

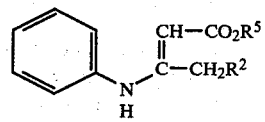

and the quinolone V produced will have the structure Va.

The carboxylic acid ester starting material XI may be prepared as described in U.S. Pat. No. 3,775,467.

Alternatively, the formula V quinolone may be prepared by reacting an isatoic anhydride

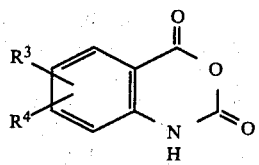

with a carboxylic acid ester XI, in a molar ratio of XII:XI of from about 0.5:1 to about 1:1, and preferably about 1:1 in the presence of an inert solvent such as tetrahydrofuran or dioxane, and a strong base such as sodium or potassium hydroxide, at a temperature ranging from about 40° to about 100° C., and preferably from about 60° to about 70° C. to form a compound of the structure XIII

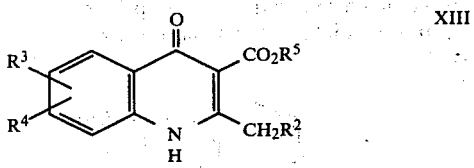

which is then hydrolyzed and neutralized to form the corresponding carboxylic acid XIV

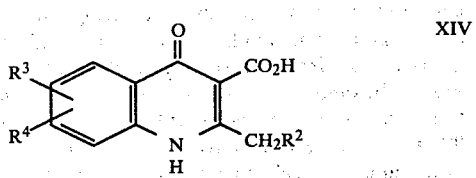

which is then decarboxylated at a temperature ranging from about 180° to about 300° C. and preferably from about 240° to about 260° C. to the formula V quinolone.

The following Examples represent preferred embodiments of the present invention.

EXAMPLE 1

β-Anilino-γ-methoxycrotonate

A solution containing 9.3 g (0.1 mol) of aniline, 14.6 g (0.1 mol) of methyl γ-methoxyacetoacetate and 1 ml of acetic acid in 100 ml of benzene is refluxed for 3 hours with azeotropic removal of water. Evaporation under reduced pressure gives 21.8 g (95%) of the crude β-anilino-γ-methoxycrotonate.

EXAMPLE 2

2-Methoxymethyl-4-quinolone

The crude crotonate (21.2 g/0.096 mol) from Example 1 is added over a 30 minute period to 75 ml of refluxing diphenyl ether. The reaction mixture is refluxed for 30 minutes, cooled, and 300 ml of hexane added. The resulting crude product is filtered, washed three times with 150 ml of hexane and dried overnight under vacuum at 60° C. Recrystallization of the crude product (15.2 g/83.5%) from water with Darco treatment gives 10.6 g (58.2%) of 2-methoxymethyl-4-quinolone as creme-colored needles, m.p. 183.5°–185.0° C.

EXAMPLE 3

2-Methoxymethylpyrazolo[1,5-c]quinazoline-5-one

A. 5-(2-Aminophenyl)-3-methoxymethylpyrazole

A mixture of 7.5 g (0.04 mol) of 2-methoxymethyl-4-quinolone, 4.2 g (0.04 mol) of hydrazine dihydrochloride, 12.8 ml (0.4 mol) of 95% hydrazine and 30 ml of ethylene glycol is slowly heated to reflux. The resulting solution is refluxed for 5 hours, cooled, diluted with 200 ml of distilled water, and extracted twice with methylene chloride (1×400 ml, 1×200 ml). The combined methylene chloride extracts are washed with 100 ml of distilled water, dried over sodium sulfate, and evaporated to 8.0 g of clear oil. Trituration with 25 ml of hexane gives 6.95 g (86%) of the 5-(2-aminophenyl)-3-methoxymethylpyrazole as a white powder, m.p. 74.0–78.0° C.

B. 2-Methoxymethylpyrazolo[1,5-c]quinazoline-5-one

A solution of 4.9 g (0.024 mol) of 5-(2-aminophenyl)-3-methoxymethylpyrazole in 135 ml of pyridine is prepared and 55 ml of a 12.5% phosgene in benzene solution is slowly added. After refluxing 22 hours, the reaction is cooled, diluted with 50 ml of distilled water, and evaporated to a dark black paste. Distilled water (200 ml) is added and the reaction mixture is extracted with methylene chloride (2×300 ml). The combined methylene chloride layers are washed with 1 N HCl (2×200 ml) and distilled water (2×200 ml). After drying over sodium sulfate, evaporation gives the crude product which is recrystallized with Darco treatment from acetonitrile to give 2.76 g (49%) of the desired ether, m.p. 192.5°–195.0° C.

EXAMPLE 4

Mixture of 2-Bromo-methylpyrazolo[1,5-c]quinazoline-5-one and 2-Hydroxymethylpyrazolo[1,5-c]quinazoline-5-one A mixture of 1.1 g (0.0048 mol) of 2-methoxypyrazolo[1,5-c]quinazoline-5-one and 15 ml of 48% HBr is refluxed for 30 minutes, cooled, and diluted by the addition of 100 ml of cracked ice and 100 ml of distilled water. The crude product is filtered and washed with 2×25 ml of cold distilled water. TLC and NMR show the crude product (1.03 g) to be a mixture of 2-hydroxymethylpyrazolo-[1,5-c]quinazoline-5-one and 2-bromo-methylpyrazolo-[1,5-c]quinazoline-5-one.

EXAMPLE 5

2-Acetyloxymethylpyrazolo[1,5-c]quinazoline-5-one

The crude product (0.9 g) from Example 4 is refluxed with 0.3 g of sodium acetate in 18 ml of acetic acid for 15.5 hours. The reaction mixture is cooled, evaporated, dissolved in 50 ml of distilled water, and extracted with methylene chloride (1×100 ml, 1×50 ml). The combined methylene chloride layers are washed with 100 ml of distilled water, dried over sodium sulfate, and evaporated to 1.01 g (81.5%) of fluffy white 2-acetyloxymethylpyrazolo[1,5-c]quinazoline-5-one, m.p. 186.0°–187.0° C.

EXAMPLE 6

2-Hydroxymethylpyrazolo[1,5-c]quinazoline-5-one

The crude acetate product from Example 5 is slurried in a solution of 0.3 g of sodium hydroxide in 10 ml of aqueous methanol (1:1). After stirring for 5 hours, the reaction mixture is neutralized with concentrated hydrochloric acid followed by the addition of 13 ml of distilled water. After stirring overnight, the product is filtered, washed with cold distilled water and dried under vacuum at 60° C. to 0.62 g (72%) of white product, m.p. 285.0°–288.0° C.

EXAMPLES 7 TO 24

Following the procedure of Examples 1 and 2 except substituting the aniline compound shown in Column I of Table A below and substituting the carboxylic acid ester shown in Column II, the intermediates shown in Columns III and IV are obtained.

TABLE A

| | Column I | | Column II | | |
|---|---|---|---|---|---|
| | $R^3$ substituted aniline | | $R^1-CH-CO_2R^5$ / $O=C-CH_2R^2$ | | |
| Ex. No. | $R^3$ (position) | $R^4$ (position) | $R^1$ | $R^2$ | $R^5$ |
| 7. | $CH_3(2)$ | H | H | $C_2H_5O$ | $CH_3$ |
| 8. | F(4) | H | $CH_3$ | $C_6H_5-CH_2O$ | $CH_3$ |
| 9. | Cl(2) | $CH_3O(4)$ | $C_2H_5$ | $C_6H_5O$ | $C_2H_5$ |
| 10. | $CH_3CO(4)$ (with =O) | H | $CH_2OH$ | $CH_3O$ | $C_2H_5$ |
| 11. | $C_6H_5-CH_2O(4)$ | H | $C_6H_5CH_2$ | $CH_3O$ | $CH_3$ |
| 12. | $C_2H_5(3)$ | $C_2H_5(4)$ | $C_6H_5$ | $C_2H_5O$ | $CH_3$ |
| 13. | $CF_3-C_6H_4$ | H | H | $C_6H_5O$ | $C_2H_5$ |
| 14. | H | H | H | $p\text{-}CH_3-C_6H_4O$ | $n\text{-}C_3H_7$ |
| 15. | H | H | $CH_3$ | $m\text{-}CH_3O-C_6H_4O$ | $i\text{-}C_3H_7$ |

| | Column III | | | | | Column IV | | | |
|---|---|---|---|---|---|---|---|---|---|
| Ex. No. | $R^3$ (position) | $R^4$ (position) | $R^1$ | $R^2$ | $R^5$ | Ex. No. | $R^3$ (position) | $R^4$ (position) | $R^1$ $R^2$ |
| 7. | as in Column I | as in Column II | | | | 16. | $CH_3(8)$ | H | as in Column II |
| 8. | | | | | | 17. | F(6) | H | |
| 9. | | | | | | 18. | Cl(8) | $CH_3O(6)$ | |
| 10. | | | | | | 19. | $CH_3C(6)$ (with =O) | H | |
| 11. | | | | | | 20. | $C_6H_5-CH_2O(6)$ | H | |
| 12. | | | | | | 21. | $C_2H_5(7)$ | $C_2H_5(6)$ | |
| 13. | | | | | | 22. | H | H | |
| 14. | | | | | | 23. | H | H | |
| 15. | | | | | | 24. | H | H | |

EXAMPLES 25 TO 33

Following the procedure of Example 3 except substituting the quinolones of Examples 16 to 24, Column IV, Table A for 2-methoxymethyl-4-quinolone, (shown in Column I of Table B below), and the cyclizing agent shown in Column II, the pyrazolo[1,5-c]quinazoline shown in Column III is obtained.

TABLE B

| | Column I | | | | Column II | Column III | | | | |
|---|---|---|---|---|---|---|---|---|---|---|
| Ex. No. | $R^3$ (position) | $R^4$ (position) | $R^1$ | $R^2$ | X ($CXCl_2$) | $R^3$ (position) | $R^4$ (position) | X | $R^1$ | $R^2$ |
| 25. | $CH_3(8)$ | H | H | $C_2H_5O$ | O | $CH_3(7)$ | H | as in Col. II | as in Col. I | |
| 26. | F(6) | H | $CH_3$ | $C_6H_5-CH_2O$ | S | F(9) | H | | | |
| 27. | Cl(8) | $CH_3O(6)$ | $C_2H_5$ | $C_6H_5O$ | O | Cl(7) | $CH_3O(9)$ | | | |
| 28. | $CH_3C(6)$ (with =O) | H | $CH_2OH$ | $CH_3O$ | S | $CH_3C(9)$ (with =O) | H | | | |
| 29. | $C_6H_5-CH_2O(6)$ | H | $C_6H_5CH_2$ | $CH_3O$ | O | $C_6H_5-CH_2O(9)$ | H | | | |
| 30. | $C_2H_5(7)$ | $C_2H_5(6)$ | $C_6H_5$ | $C_2H_5O$ | S | $C_2H_5(8)$ | $C_2H_5(9)$ | | | |
| 31. | H | H | H | $C_6H_5O$ | O | H | H | | | |
| 32. | H | H | H | $p\text{-}CH_3-C_6H_4O$ | S | H | H | | | |

TABLE B-continued

| | Column I | | | | Column II | Column III | | | | |
|---|---|---|---|---|---|---|---|---|---|---|
| Ex. No. | $R^3$ (position) | $R^4$ (position) | $R^1$ | $R^2$ | $CXCl_2$ X | $R^3$ (position) | $R^4$ (position) | X | $R^1$ | $R^2$ |
| 33. | H | H | $CH_3$ | $m$-$CH_3O$—$C_6H_4O$ | O | H | H | | | |

EXAMPLES 34 TO 42

Following the procedure of Examples 4 and 5, except substituting the quinazoline of Examples 25 to 33 (shown in Column I of Table C below) and substituting for the sodium acetate and acetic acid, the salt and acid shown in Column II, the quinazoline shown in Column III is obtained.

EXAMPLES 43 TO 51

Following the procedures of Example 6 except substituting the quinazolines of Examples 34 to 42 (shown in Column I of Table D below), the corresponding hydroxymethyl compound shown in Column II is obtained.

TABLE C

Column I — structure with $R^1$, $CH_2R^2$, $R^3$, $R^4$, X, pyrazole/quinazoline core Column II — MOCR (O=C), RCOOH

| Ex. No. | $R^3$(position) | $R^4$(position) | X | $R^1$ | $R^2$ | R | M |
|---|---|---|---|---|---|---|---|
| 34. | $CH_3$(7) | H | O | H | $C_2H_5O$ | $CH_3$ | K |
| 35. | F(9) | H | S | $CH_3$ | $C_6H_5$—$CH_2O$ | $C_2H_5$ | Na |
| 36. | Cl(7) | $CH_3O$(9) | O | $C_2H_5$ | $C_6H_5O$ | $C_6H_5$ | Na |
| 37. | $CH_3C(9)$ (O=) | H | S | $CH_2OH$ | $CH_3O$ | $C_6H_5CH_2$ | Na |
| 38. | $C_6H_5$—$CH_2O$(9) | H | O | $C_6H_5CH_2$ | $CH_3O$ | $n$-$C_4H_9$ | K |
| 39. | $C_2H_5$(8) | $C_2H_5$(9) | S | $C_6H_5$ | $C_2H_5O$ | $n$-$C_3H_7$ | K |
| 40. | H | H | O | H | $C_6H_5O$ | $C_2H_5$ | Na |
| 41. | H | H | S | H | $p$-$CH_3$—$C_6H_4O$ | $CH_3$ | Na |
| 42. | H | H | O | $CH_3$ | $m$-$CH_3O$—$C_6H_4O$ | $C_2H_5$ | K |

Column III — structure with $CH_2OCR$ (O=)

| Ex. No. | $R^3$(position) | $R^4$(position) | $R^1$ | X | R |
|---|---|---|---|---|---|
| 34. | as in Column I | | | as in Column II | |
| 35. | | | | | |
| 36. | | | | | |
| 37. | | | | | |
| 38. | | | | | |
| 39. | | | | | |
| 40. | | | | | |
| 41. | | | | | |
| 42. | | | | | |

TABLE D

| Ex. No. | R³(position) | R⁴(position) | X | R¹ | R | R³(position) | R⁴(position) | R¹ | X |
|---|---|---|---|---|---|---|---|---|---|
| 43. | $CH_3$(7) | H | O | H | $CH_3$ | as in Column I | | | |
| 44. | F(9) | H | S | $CH_3$ | $C_2H_5$ | | | | |
| 45. | Cl(7) | $CH_3O$(9) | O | $C_2H_5$ | $C_6H_5$ | | | | |
| 46. | $CH_3\overset{O}{\underset{\parallel}{C}}$(9) | H | S | $CH_2OH$ | $C_6H_5CH_2$ | | | | |
| 47. | $C_6H_5$-$CH_2O$(9) | H | O | $C_6H_5CH_2$ | n-$C_4H_9$ | | | | |
| 48. | $C_2H_5$(8) | $C_2H_5$(9) | S | $C_6H_5$ | n-$C_3H_7$ | | | | |
| 49. | H | H | O | H | $C_2H_5$ | | | | |
| 50. | H | H | S | H | $CH_3$ | | | | |
| 51. | H | H | O | $CH_3$ | $C_2H_5$ | | | | |

What is claimed is:

1. An intermediate of the structure

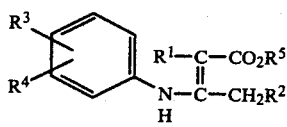

wherein $R^1$ is hydrogen, lower alkyl, hydroxymethyl, phenyl-lower alkyl, phenyl or phenyl substituted with halogen, lower alkyl, lower alkoxy, or trifluoromethyl;

$R^2$ is lower alkoxy, phenyl-lower alkoxy, phenoxy, or phenoxy substituted with lower alkyl or lower alkoxy;

$R^3$ and $R^4$ are the same or different and are selected from the group consisting of hydrogen, alkyl of 1 to 4 carbons, alkoxy of 1 to 4 carbons, lower alkanoyloxy of 1 to 4 carbons, nitro, benzyloxy, benzyloxy having a single mono-lower alkoxy substituent, halogen, hydroxy, and trifluoromethyl;

and $R^5$ is lower alkyl.

2. The intermediate as defined in claim 1 wherein $R^1$, $R^3$ and $R^4$ are H.

3. The intermediate as defined in claim 1 having the structure

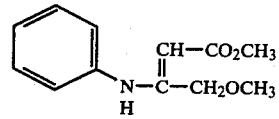

* * * * *

UNITED STATES PATENT AND TRADEMARK OFFICE
CERTIFICATE OF CORRECTION

PATENT NO. : 4,303,795          Page 1 of 2
DATED : December 1, 1981
INVENTOR(S) : Richard A. Conley, et al.

It is certified that error appears in the above-identified patent and that said Letters Patent are hereby corrected as shown below:

Column 1, line 5, "56,600" should read --56,660--.
Column 1, line 37, "reated" should read --related--.
Column 2, structure IV should read -- 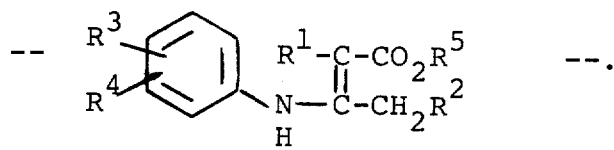 --.

Column 3, line 48, "wher" should read --where--.
Columns 9 and 10, TABLE A, Column III, under headings "$R^3$ (position)  $R^4$ (position)" insert --⌣--; and under headings "$R^1$  $R^2$  $R^5$" insert --⌣--; in Column IV, under headings "$R^1$  $R^2$" insert --⌣--.
Columns 9 and 10, TABLE B, Column III, under heading "X" insert --⌣--; and under headings "$R^1$  $R^2$" insert --⌣--.
Columns 11 and 12, TABLE B, Column III, under the heading "X" insert --⌣-- as in Col. II; and under the headings "$R^1$  $R^2$" insert --⌣-- as in Col. I.
Column 12, line 18, "procedures" should read --procedure--.

UNITED STATES PATENT AND TRADEMARK OFFICE
CERTIFICATE OF CORRECTION

PATENT NO. : 4,303,795            Page 2 of 2

DATED : December 1, 1981

INVENTOR(S) : Richard A. Conley, et al.

It is certified that error appears in the above-identified patent and that said Letters Patent are hereby corrected as shown below:

Columns 11 and 12, TABLE C, Column III, under headings "$R^3$(position)   $R^4$(position)   $R^1$   X" insert -- ⌒⌒⌒ --;

and under heading "R" insert -- ⌒⌒⌒ --.

Columns 13 and 14, TABLE D, Column II, under headings "$R^3$(position)   $R^4$(position)   $R^1$   X" insert -- ⌒⌒⌒ --.

Signed and Sealed this

Twenty-ninth Day of June 1982

[SEAL]

*Attest:*

*Attesting Officer*

GERALD J. MOSSINGHOFF

*Commissioner of Patents and Trademarks*